US009835561B2

(12) United States Patent
Di Fabrizio et al.

(10) Patent No.: US 9,835,561 B2
(45) Date of Patent: Dec. 5, 2017

(54) ANALYTIC DEVICE INCLUDING NANOSTRUCTURES

(71) Applicant: KING ABDULLAH UNIVERSITY OF SCIENCE AND TECHNOLOGY, Thuwal (SA)

(72) Inventors: Enzo Di Fabrizio, Thuwal (SA); Andrea Fratalocchi, Thuwal (SA); Juan Sebastian Totero Gongora, Thuwal (SA); Maria Laura Coluccio, Catanzaro (IT); Patrizio Candeloro, Catanzaro (IT); Gianni Cuda, Catanzaro (IT)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 15/108,225

(22) PCT Filed: Dec. 23, 2014

(86) PCT No.: PCT/IB2014/003194
§ 371 (c)(1),
(2) Date: Jun. 24, 2016

(87) PCT Pub. No.: WO2015/097559
PCT Pub. Date: Jul. 2, 2015

(65) Prior Publication Data
US 2016/0327486 A1    Nov. 10, 2016

Related U.S. Application Data

(60) Provisional application No. 61/920,725, filed on Dec. 24, 2013.

(51) Int. Cl.
*G01J 3/44*    (2006.01)
*G01N 21/65*    (2006.01)
(Continued)

(52) U.S. Cl.
CPC ............ *G01N 21/658* (2013.01); *B82Y 20/00* (2013.01); *G01N 21/648* (2013.01)

(58) Field of Classification Search
CPC ... G01J 3/44; G01J 3/02; G01N 21/64; G01N 21/65; G01N 21/68; B82Y 20/00
See application file for complete search history.

(56) References Cited

U.S. PATENT DOCUMENTS

2006/0050268 A1    3/2006 Talley
2012/0062884 A1*    3/2012 Sakagami ............ G01J 3/0224
356/301

FOREIGN PATENT DOCUMENTS

WO    2010/079410    7/2010

OTHER PUBLICATIONS

International Search Report dated Jun. 11, 2015, issued in International Application No. PCT/IB2014/003194.
(Continued)

*Primary Examiner* — Abdullahi Nur
(74) *Attorney, Agent, or Firm* — Hamingway & Hansen, LLP; D. Scott Hemingway

(57) ABSTRACT

A device for detecting an analyte in a sample comprising: an array including a plurality of pixels, each pixel including a nanochain comprising: a first nanostructure, a second nanostructure, and a third nanostructure, wherein size of the first nanostructure is larger than that of the second nanostructure, and size of the second nanostructure is larger than that of the third nanostructure, and wherein the first nanostructure, the second nanostructure, and the third nanostructure are positioned on a substrate such that when the nanochain is excited by an energy, an optical field between the second nanostructure and the third nanostructure is stronger than an optical field between the first nanostructure and the second nanostructure, wherein the array is configured to receive a
(Continued)

sample; and a detector arranged to collect spectral data from a plurality of pixels of the array.

20 Claims, 19 Drawing Sheets

(51) Int. Cl.
 *B82Y 20/00* (2011.01)
 *G01N 21/64* (2006.01)

(56) References Cited

OTHER PUBLICATIONS

Written Opinion of the International Searching Authority dated Jun. 11, 2015, issued in International Application No. PCT/IB2014/003194.
Kuiru Li et al: "Self-similar chain of metal nanospheres as an efficient nanolens", Physical Review Letters, American Physical Society, vol. 91, No. 22, Nov. 26, 2003 (Nov. 26, 2003).

* cited by examiner

ANALYTIC DEVICE INCLUDING NANOSTRUCTURES

PRIORITY CLAIM

This application claims the benefit under 35 USC 371 to International Application No. PCT/IB2014/003194, filed Dec. 23, 2014, which claims priority to U.S. Provisional Patent Application No. 61/920,725, filed Dec. 24, 2013, each of which is incorporated by reference in its entirety.

TECHNICAL FIELD

The invention relates to a device that uses nanostructures to analyze samples.

BACKGROUND

Raman spectroscopy is a technique that utilizes Raman scattering by molecules to assess the molecules and allow the molecules to be identified by spectral signature patterns.

SUMMARY

In one aspect, a device for detecting an analyte in a sample can include an array including a plurality of pixels, each pixel including a nanochain comprising a first nanostructure, a second nanostructure, and a third nanostructure, wherein size of the first nanostructure is larger than that of the second nanostructure, and size of the second nanostructure is larger than that of the third nanostructure, and wherein the first nanostructure, the second nanostructure, and the third nanostructure are positioned on a substrate such that when the nanochain is excited by an energy, an optical field between the second nanostructure and the third nanostructure is stronger than an optical field between the first nanostructure and the second nanostructure, wherein the array can be configured to receive a sample; and a detector arranged to collect spectral data from a plurality of pixels of the array.

In certain embodiments, the first nanostructure can include a metal, the second nanostructure can include a metal, and the third nanostructure can include a metal. The nanostructure can include silver, gold, platinum, or aluminum.

In certain embodiments, the second nanostructure can be positioned between the first nanostructure and the third nanostructure. The distance between the first nanostructure and the second nanostructure can be less than the diameter of the second nanostructure. The distance between the second nanostructure and the third nanostructure can be less than the diameter of the third nanostructure.

The device can include 10 by 10 pixels. The distance between two pixels can be at least 1 μm. Each pixel can deliver spectral data for at least one analyte. Each pixel can be capable of detecting at least two different kinds of analytes. The device can be capable of detecting at least 5 different kinds of analytes. The device can be capable of detecting at least 10 different kinds of analytes. The device can be capable of detecting at least 20 different kinds of analytes.

In certain embodiments, the analyte can be detectable by Raman spectrum. The analyte can be a peptide. The device can be capable of detecting a single molecule.

In certain embodiments, the first nanostructure is a nanosphere, the second nanostructure is a nanosphere, and the third nanostructure is a nanosphere. The diameter of the first nanostructure can be less than 500 nm. The diameter of the second nanostructure can be less than 200 nm. The diameter of the second nanostructure can be less than 100 nm.

In another aspect, a method for detecting an analyte can include contacting an analyte with an array including a plurality of pixels, each pixel including a nanochain comprising a first nanostructure, a second nanostructure, and a third nanostructure, wherein size of the first nanostructure is larger than that of the second nanostructure, and size of the second nanostructure is larger than that of the third nanostructure, and wherein the first nanostructure, the second nanostructure, and the third nanostructure are positioned on a substrate such that when the nanochain is excited by an energy, an optical field between the second nanostructure and the third nanostructure is stronger than the optical field between the first nanostructure and the second nanostructure; and collecting spectral data from a plurality of pixels of the array.

In certain embodiments, the method can include taking Raman spectrum of the nanochain. The analyte can include a peptide. The first nanostructure can include a metal, the second nanostructure can include a metal, and the third nanostructure can include a metal. The nanostructure can include silver, gold, platinum, or aluminum. In certain embodiments, the second nanostructure can be positioned between the first nanostructure and the third nanostructure.

In certain embodiments, the method can detect a single molecule.

Other aspects, embodiments, and features will be apparent from the following description, the drawings, and the claims.

DETAILED DESCRIPTION

Figure 1A:
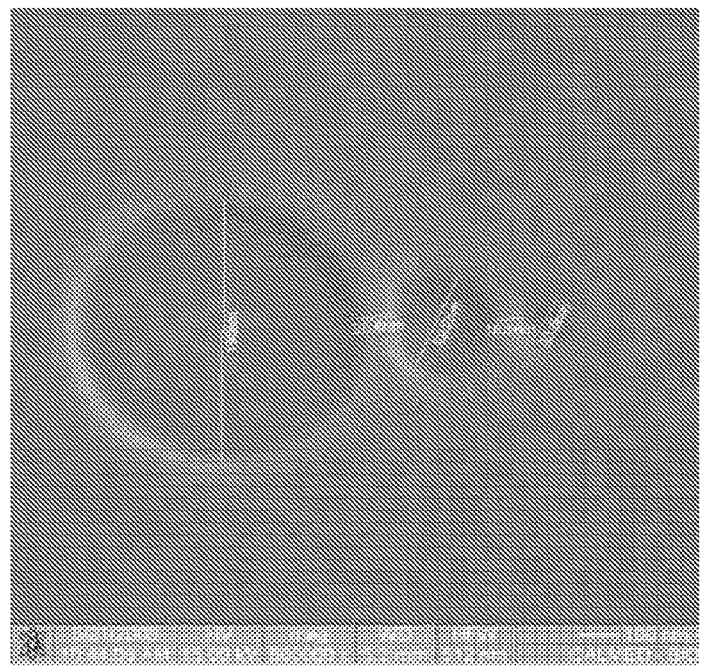
FIG. 1A shows an SEM image of a patterned area and FIG. 1B shows the nanochain after electroless growth.

Nano-optics system offers a great possibility to control the propagation of light at the surface of nanometals due to the fact that nanometallic structure overcomes the diffraction limit, observed in the conventional optics.

A device for detecting an analyte can include a nanochain comprising of three nanostructures. The device can also include a plurality of pixels, where each pixel includes at least one nanochain. A nanochain can include a first nanostructure, a second nanostructure, and a third nanostructure. The nanostructures can be aligned with decreasing size. For example, size of the first nanostructure can be larger than that of the second nanostructure, and size of the second nanostructure can be larger than that of the third nanostructure. The second nanostructure can be positioned between the first nanostructure and the third nanostructure.

The nanostructures can be a metal. At visible regime, a noble metal can be preferred, such as a silver or a gold, or others. In the ultra violet regime, the metal can be a noble metal, such as silver, and the metal can be other type of metal, such as aluminum. When a nanochain is excited by an energy, an optical field or an electric field between the second nanostructure and the third nanostructure can be stronger than the field between the first nanostructure and the second nanostructure.

The device can include any number of pixels, for example 10×10 pixels. The distance between the pixels can be controlled such that the device can provide a detection signal for only one pixel. In one example, the distance between the pixels can be at least 1 µm. The distance between the nanostructures can also be controlled with precision of nanometers.

The device can detect an analyte by Raman and/or fluorescence spectroscopy. The analyte can include a peptide. The device can detect a mixture including more than one type of analyte, such as 20 peptides. The device can also detect the existence or absence of a single molecule.

Surface Enhanced Raman Spectroscopy (SERS)

The intensity of a Raman spectrum of a molecule that is in close proximity to an appropriate noble metal surface can be remarkably larger than in the absence of the surface. This phenomenon can be due to light excitation of charge density fluctuations on the metallic surface, which in turn creates a strong electromagnetic field nearby. The frequency of the radiated field can be close to that of the incident light, while, spatially, the field can be characterized by strongly localized regions of low and high intensity (higher than the intensity of the incident light). A molecule can emit Raman scattered light with a magnitude proportional to the fourth power of the local value of the field.

The overall enhancement in Raman signal from a molecule located in a high intensity region near the surface can exceed eight orders of magnitude. Furthermore, the strong localization of the enhancement regions makes it possible to resolve Raman signal from objects of length scales comparable to that of these regions.

The field distribution that radiates from a surface can depend on the geometry of the SERS device. In one example, nanostructures can be formed by aligning three metal nanostructures, such as silver nanospheres, of decreasing diameter. A dramatic increase in field intensity can be obtained in the gap between the two smaller nanostructures. The gap can be 5-20 nm wide. A device with such an alignment can have a tunable spectral maximum for the enhancement.

Preparation of a Nanochain

The progress in plasmonics device architecture has also been supported by the advancement in the nanofabrication techniques. With the fast development of plasmonics area and the application of nanoplasmonic device, from physics to biology and engineering to medical field, it can be important to fabricate a device that demonstrates the generation of high electromagnetic field to analyze a substance, for example, using spectroscopic techniques. The device reproducibility is important as well.

There are many routes to fabricate SERS devices, such as metal island films, such as electrochemically modified electrodes, nanosphere lithography, electron beam lithography, etc. See, for example, Costantino et al, Anal. Chem. 73, 2001, 3674-3678; D L Jeanmaire et al., J. Electroanal. Chem. 84, 1977, 1, each of which is incorporated by reference in its entirety. One way is to produce Ag colloids and then attach these metal colloids to biomolecules. See, for example, K. Kneipp et al, *Phys. Rev. Letts.* 78, 1997, 1667, which is incorporated by reference in its entirety. Continuous spectral fluctuations in Raman intensity can be observed at different times for SERS substrates. In other terms, SERS substrate prepared by utilizing colloidal technique can show statistical signal variations. Efforts are being made to the periodic reproducible and controllable SERS substrates, which have been utilized to carry out the analysis for various molecules (Rhodamine6G, protein, etc.). See, for example, G. Das et al., *Biosensors and Bioelectronics,* 24, 2009, 1693-1699; F. De Angelis et al., *Nano Letts.* 8(8), 2008, 2321-2327, each of which is incorporated by reference in its entirety. Another kind of SERS device can be fabricated. See, for example, K. Li et al., *Phys. Rev. Letts.* 91 (2003) 227402; J. Dai, et al., *Phys. Rev. B* 77 (2008) 115419, each of which is incorporated by reference in its entirety.

A nanochain includes at least three nanostructures. A nanostructure is a structure with a size of less than 1 µm. A nanostructure can be a nanolense, a nanosphere, and so on. In one example, a nanochain can include three nanostructures aligned with decreasing size. A nanochain can be prepared via the combination of high precision electron beam lithography and electroless plating.

Electroless growth is a process where metal ions are reduced and deposited as metals upon a pre-prepared silicon surface. Metal grains may be accordingly obtained with an average size as small as few nanometers, with an overall shape and dimension that can be regulated with a high precision and reproducibility.

Building the nanostructures can include several steps requiring high performance fabrication technologies. First, the nanostructure pattern can be fabricated in a film of polymethylmethacrylate (PMMA-A2) polymer (the resist) coated onto a silicon surface. The pattern can include three aligned cylindrical cavities of different diameters; the first cavity can have a diameter of between 500 to 100 nm; the second cavity can have a diameter of between 200 and 50 nm; the third cavity can have a diameter of between 100 and 5 nm. The height of the cavities can be between 20 and 150 nm. These cavities can be at different distances. For example, the distance between the first cavity and the second cavity can be between 10-100 nm, and the distance between the second cavity and the third cavity can be 5-50 nm.

The pattern can be realized using an ultra-high-resolution electron-beam lithography (EBL) technique. In EBL, a highly focused electron-beam is used to depolymerize regions of the resist of controlled geometry. The depolymerized part of the resist can be then developed by immersion in an appropriate solvent and a mold for the successive deposition of a metal, such as a silver, is obtained. The features of a mold used for this can be controlled. After patterning with EBL and rinsing, a highly clean silicon surface can be obtained inside cavities.

This process can include immersing the nanostructure pattern in a water solution containing a metal salt, such as $AgNO_3$, and an acid, such as HF. The acid can react with the $SiO_2$ on the surface of the exposed silicon at the bottom of the cavities and initiates a series of steps that eventually leads to transferring electrons from the solution to the silicon. The metal ions from the dissociated salt that diffuse to the surface can be reduced by these electrons to Ag which is adsorbed on the surface via ionic interactions. The metallic Ag structures that grow via these steps can act as an electrode charged by the electrons in the silicon and further contribute to the reduction of silver ions from the solution. Since no external electrical field is required to drive these reactions, this type of deposition process is usually referred to as electroless plating. After the deposition of metal particles, the sample can be rinsed with bi-distilled water to wash out the salt from the nanostructure's surface.

Optical properties of nanoparticles, such as metallic nanoparticles, and their aggregates can be interesting. Such nanoparticles can induce local optical fields that exceed the exciting fields. Raman scattering can be increased, which allows for the detection and spectroscopy of single molecules. The Raman enhancement can be proportional to the fourth power of the local field. Enhanced Raman scattering can exist at the gaps between metal nanostructures.

A Device Including a Nanochain

Nanostructure plasmonic devices, based on nanoholes, nanoantenna, nanocolloids, metal nanoparticles (in particular, gold, silver, or platinum) of varying shape, size, size distribution, etc., have been proposed to enhance the optical signals of interested molecules, attached or located in close proximity to nanometer-sized metallic structure. See, for example, M. Moskovits, *Rev. Mod. Phys.* 57, 1985, 783; J J Mock, et al., J. Chemical Physics, 116, 2002, 6755, each of which is incorporated by reference in its entirety. When laser radiation interacts with sharp metallic surfaces, the increase in localized electric field can induce an enhancement in the Raman signal. The increase in Raman scattering may be large. See, for example, K. Kneipp, et al., *Phys. Rev. Letts.* 78, 1997, 1667; S. Nie, et al., *Science* 275, 1997, 1102, each of which is incorporated by reference in its entirety. The increase delivers the possibility of detecting very little amount of molecules, at the limit of single molecule situated in the proximity of the metallic surface.

For metal having resonant quality factor 'Q' and number of nanosphere 'n', the theoretical effective SERS enhancement $G_{SERS}$ can be $Q^{4n}$. When considering Ag-based nanochains (Q~30) constituted by three nanospheres, the theorectical SERS enhancement factor can be in the order of $10^{12}$ or more. An SERS device can be made of a self-similar chain. A self-similar chain can be a chain including nanospheres where the ratios between the subsequent radiuses and gaps are constant. A nanochain can include three metal nanospheres. Two techniques (e-beam lithography technique and metal electroless deposition) can be combined to fabricate this device. The use of well-defined nanolithographic structures allows a better control of the SERS substrate, giving the possibility to fabricate a controllable and reproducible device. To satisfy the inflexible nanostructure size and shape, electron beam lithography technique can be taken into consideration. Whereas, the site-selective silver nanoparticle using electroless deposition technique can be utilized for augmenting the electromagnetic field. Theoretical simulation using Finite Difference Time Domain (FDTD) can be performed for the self-similar nanochain SERS device, keeping the real characteristic parameters; dielectric constant of the polymer, Q factor of silver, the experimentally observed the size of the nanospheres and the distance between the two consecutive silver nanospheres, etc. and is found to have enhancement factor about $10^7$-$10^8$. This signal enhancement value is close to what it is observed by self-similar nanochains SERS substrate fabricated after depositing various molecules on it.

Nanochain SERS biophotonics device can be designed and fabricated. The device exhibits the few molecules detection capabilities for Rhodamine 6G (R6G), site selective deposited carbon, DNA, control and mutated BRCA peptide. In this nano-optics system, electro-magnetic light confines efficiently in the gap between the two smallest Ag nanospheres due to localized surface plasmon in such a manner that it leads to a nanolocalization of e.-m. field and so the Raman signal intensity.

An analytical device can include a nanochain comprising nanostructures. The nanostructures are metallic. The material that can be used includes silver, gold, aluminum. The nanostructures can be in an array of three, aligned with decreasing size. The surface and shape of nanostructures can be disordered (the nominal center of gravity of each nanostructure can be aligned with an accuracy better than 2 nm). The analytical device can be used to detect an analyte. The analytical device can be used for generic molecules and in particular for protein detection from a sample, such as a human sample. The device can include a plurality of pixels. The pixels can form an array. Each pixel can be the sensitive unit of the device. The device can produce a strong localization of electrical field when the nanochain is illuminated by a laser light. Various laser wavelength regimes, such as visible wavelength regime, can be used. A nanochain can include three nanospheres. The localization of the electrical field can be mainly between the smallest sphere and the middle sphere. In a three-nanostructure chain aligned with decreasing size, the electrical field between the smallest nanostructure and the mid-sized nanostructure can be stronger than that between the largest nanostructure and the mid-sized nanostructure.

A nanochain can generate a localized electrical field when illuminated by a laser beam. If molecules are deposited on the nanochain, they scatter the laser light that can be analysed and detected by a Raman spectroscope apparatus. The information obtained by this apparatus can be a specific signature of the molecule that entered the sensitive area of the nanochain.

A nanochain array can be fabricated and used to analyse a material. The material can be a mixture including at least one type of analyte. For example, a nanochain array can detect a mixture of about 20 peptides from a human sample of breast cancer. The mixture can be resolved component by component.

The footprint of the electrical field can cover a region, whose size can be about 5×5 $nm^2$. This indicates that if a solute is deposited on a nanochain, only the molecules that enter this region can be detected. The device may not be able to detect molecules outside of this region. The molecules can be detected through a spectroscopy, such as a Raman spectroscopy.

The device can detect and analyze composition of highly diluted mixtures of molecules, such as in the range of nanomolar. This can be applied to early cancer diagnosis or pollutant environmental analysis and others. The device can be used when there is a mixture of soluble molecules in a generic solvent and the detection can be combined with a spectroscopy technique such as Raman or Fluorescence. The sample can be a diluted sample. The dilution factor can be such that the concentration of an analyte of interest in the sample leads to a significant probability that one molecule can be found at a "hot spot" (the sensitive region) of the nanolens. The measured experimental deposition rate in the hot spot is between 0.25 to 1%. This means that even if 99% of molecules go outside the hot spot, the sensitivity of the nanochain allows the detection. This does not require sophisticated means or tools to deposit the molecules exclusively in the hot spot area. For example, an analyte concentration can be between 1 and 100 nanomolar, for example between 2 nanomolar and 25 nanomolar. This can be a range used with a device including a nanochain.

The further improvement in the functioning of the device can be due to the intrinsic disorder or roughness of a surface of each nanosphere. This disorder can contribute to a larger localization of the electrical field.

The working principle of the device can be due to plasmonics and nano-localization of electrical field for obtaining a strong Raman signal even with few molecules in the pixel. It can further exploit the natural disorder arising in the fabrication of the nanospheres to greatly enhance the electric field and achieve a high sensitivity. The scale of sensitive area can be strongly localized. The device can solve highly diluted mixture by physical means, label free with no additional chemical reactions to detect the composition of the solute. The design and the use of the array can solve a mixture of peptides that bring the signature of a tumor. The reconstruction of mixture composition can be realized by reading the Raman spectra of each pixel in the matrix array. With proper dilution, each pixel can contain, randomly distributed, only part of the mixture component. Reading all pixels, all components of the mixture can be recovered. Typically in each pixel, between 2 to 4 components dominate. These are weighted by a linear combination of pure components. The operation is repeated on each pixel.

The advantages of the device include that it is sensitive to low concentration of solute down to nanomolar, it gives a lot of information on the chemical state of the molecules composing the mixture, such as a wild type or a mutated form of peptides, and the quantity of solute can be very low, such as below the nanogram range.

Examples

The device fabrication can involve several steps requiring high performance fabrication technologies. The nanochain pattern can be written using an ultra-high-resolution e-beam lithography (EBL) technique, realized on a thin layer of PMMA-A2 resist (50 nm), which is spun onto a cleaned silicon substrate. The stability of the beam and its settings (45 pA of beam current at 50 keV acceleration voltage, beam size—2 nm) generated by EBL system (CRESTEC CABL-9000C), the features of the resist used, and the development process (1 min rinsing with IPA at 4° C.) help produce a controllable nanostructure. The dimension of the patterned SERS device is around 320 nm and the two small gaps between the two consecutive nanospheres are 20.6 nm and 18.5 nm, respectively, as shown in FIG. 1A). The smallest nanohole on resist is of 33.6 nm diameter. Various kinds of nanochains structures with single, double, quadruple lenses are fabricated in order to test and compare the capability to localize the Plasmon Polaritons (PPs) close to the smallest nanospheres.

Figure 1B:
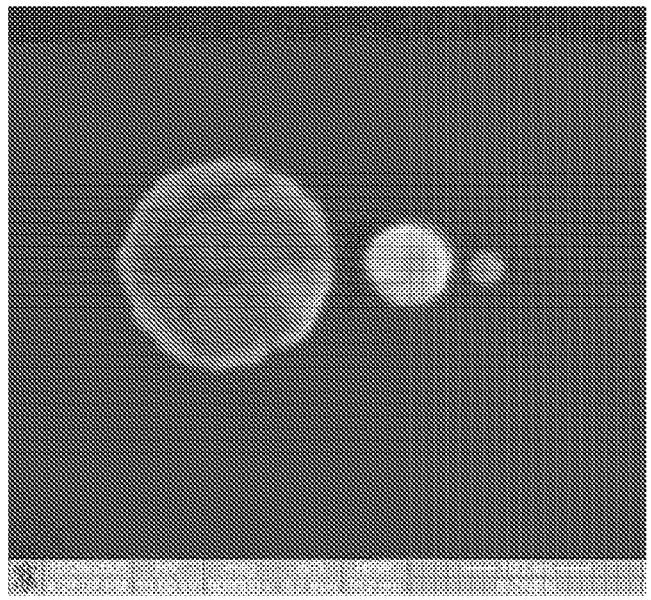
Figure 2A:
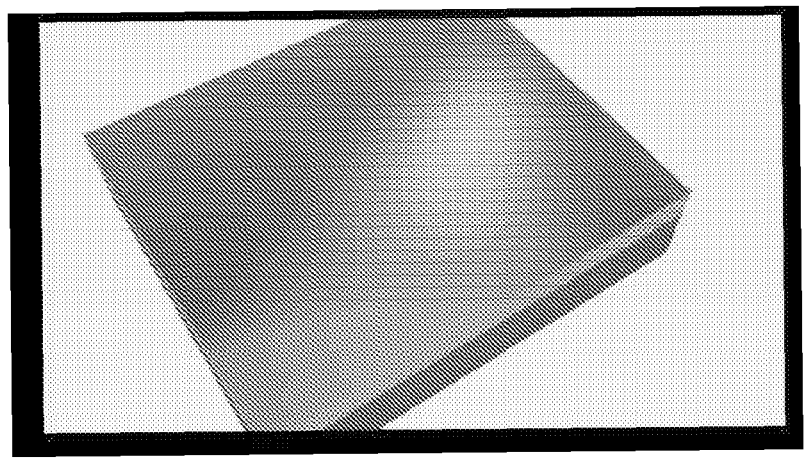
FIGS. 2A-2D show a schematic representation of a nanochain formation.
Figure 2B:
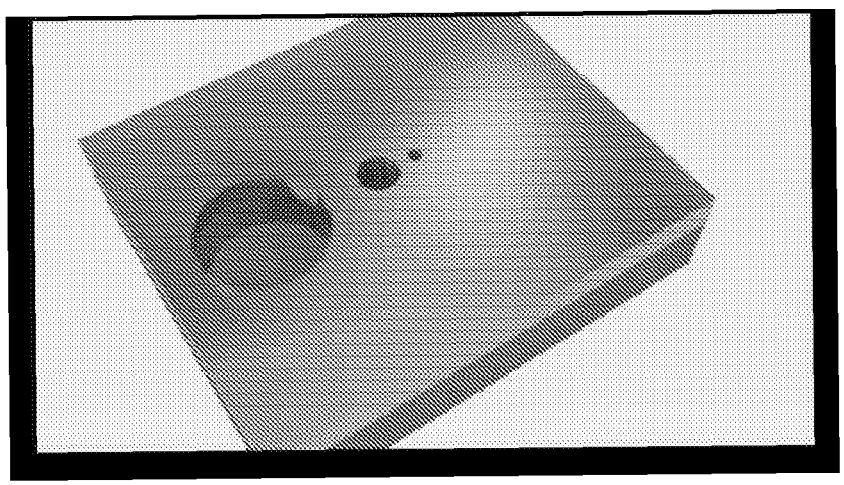
Figure 2C:
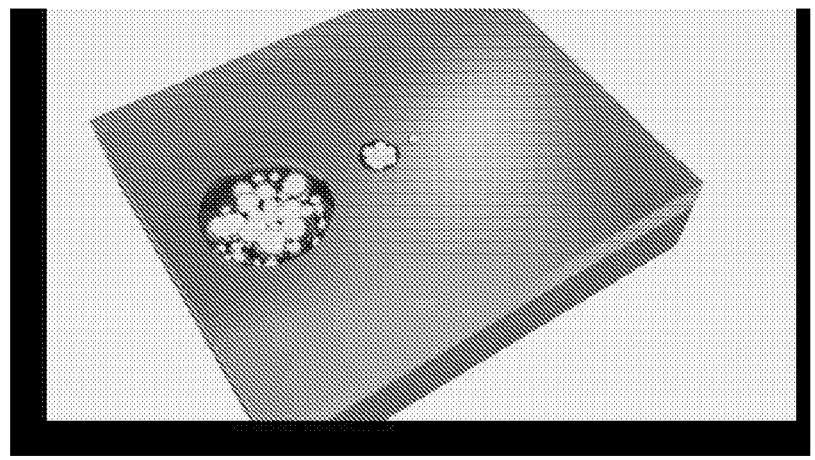
Figure 2D:
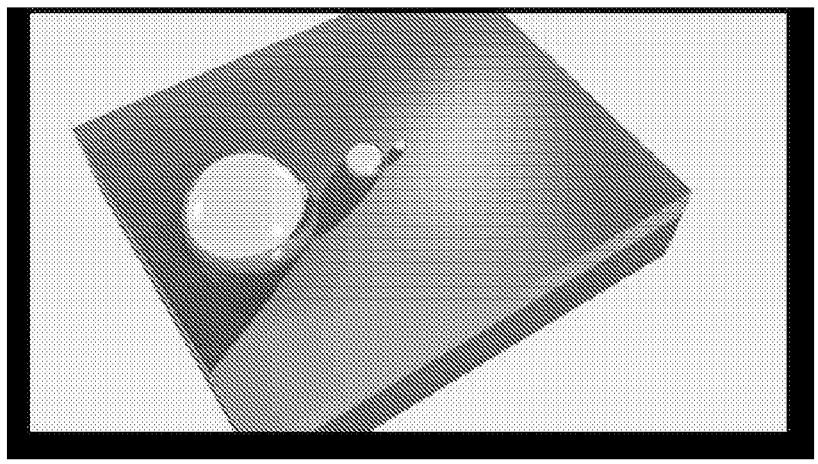
Figure 10A:
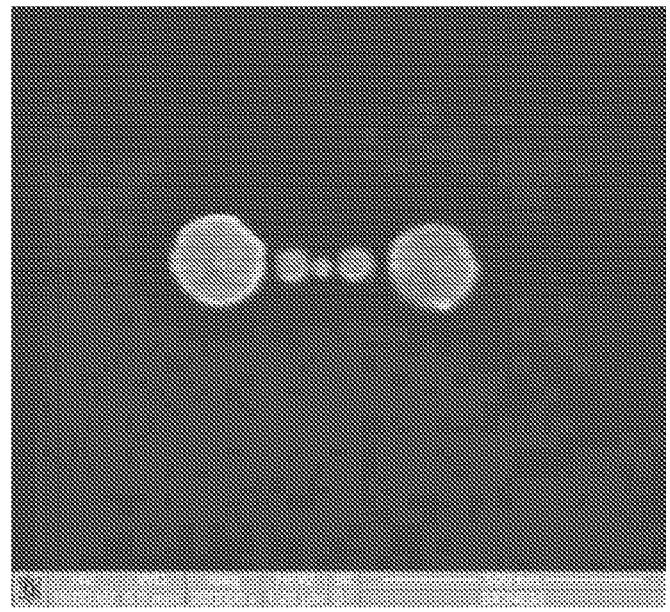
FIGS. 10A-10C shows SEM images of nanostructures with different sizes and numbers on nanochains (monomer, dimer, trimer tetramer).
Figure 10B:
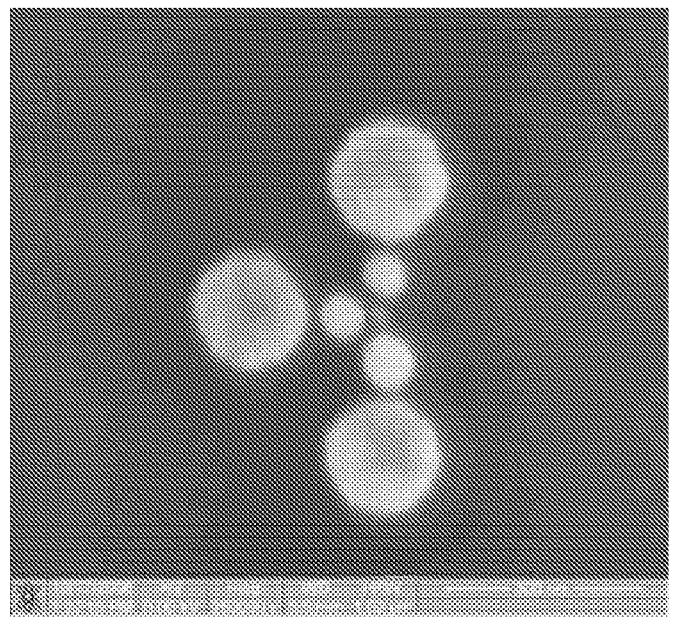
Figure 10C:
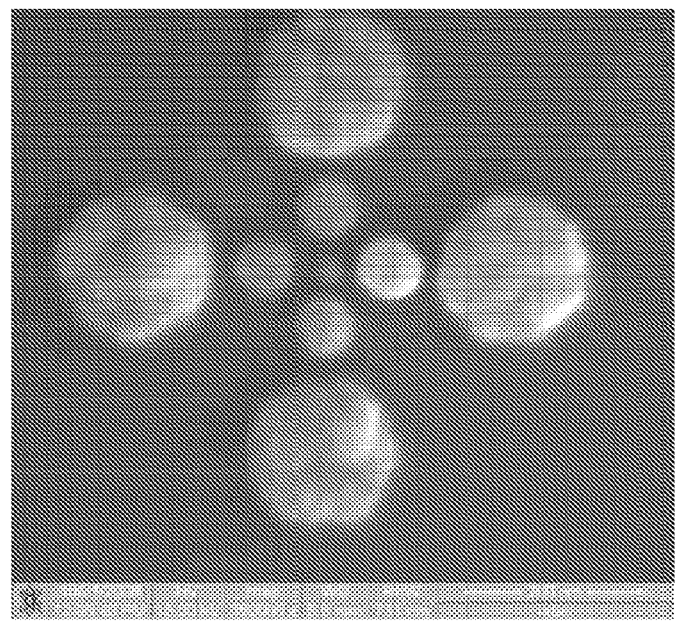

The strategy to perform a highly controlled nanochemistry over the post-lithographic surface was an important step to make a site-selective metal deposition. The electroless process can be used to deposit Ag-metal on a predefined area in which the reduction of oxidized metallic species led to formation of neutral metal atom. See, for example, D. V. Goia, et al., New J. Chem. 22, 1998, 1203, which is incorporated by reference in its entirety. Ag-nanometal deposition can be accomplished using the solution of $AgNO_3$ and HF. See, for example, S. Yae et al, Electrichimica Acta 53, 2007, 35, which is incorporated by reference in its entirety. Right after the deposition of metal particles, the sample was rinsed with bidistilled water to wash out the salt from the nanostructure surface. After the Ag-electroless deposition, the two small gaps between the lenses are 37.7 nm and 8.85 nm, whereas the diameter of smallest nanosphere becomes 25.8 nm, shown in FIG. 1B. Nanostructure devices with two, three and four nanochains can also be prepared, as shown in FIGS. 10A-10C. A pixel of a chip can include 2 nanochains (a dimer), 3 nanochains (a trimer), or 4 nanochains (a tetramer). The fabrication process in summary is also illustrated in FIGS. 2A-2D. After the resist spin coating (FIG. 2A), the lithography process creates nanohole (FIG. 2B), which can be further used for metal site-selective deposition. The desposition in the nanohole (FIG. 2C) ultimately forms the self-similar nanochain substrate (FIG. 2D). Au-based nano-optics devices can also be fabricated following the same technique.

The device can be used as an SERS device. Micro-Raman spectra (inVia Raman Microscope, Renishaw) of the device were excited by using 514 nm Ar+ laser (Power=0.018 mW and accumulation time=4 sec) in backscattering geometry with the spectral resolution of about 1.3 $cm^{-1}$. High magnification objective 150× is used for all the Raman measurements. XY Raman mapping measurements were carried out with the minimum step size of 100 nm.

Figures 3A, 3B:
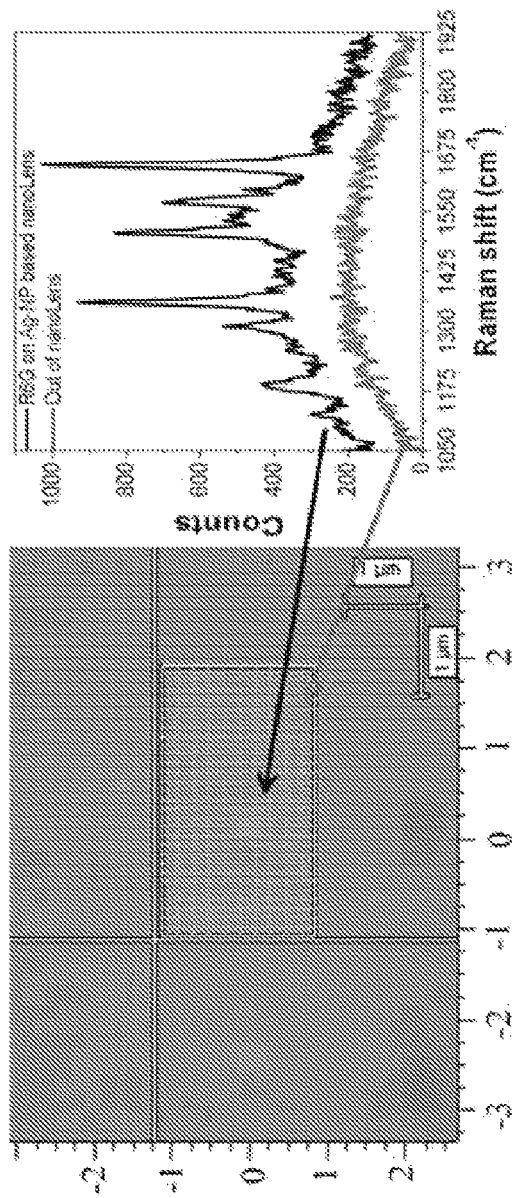
FIG. 3A shows an optical image of a scanned area on a device containing a nanochain.
FIG. 3B shows spectra measured at different positions of the device.

R6G (an organic fluorescent molecule) monolayer was deposited over the device using immersion technique and thereafter it was rinsed by bidistilled water to wash out the excess molecules not deposited directly on the metal surface. Micro-Raman measurements are performed in the area that consists of one nanochain structure, shown in FIG. 3A. Two static Raman spectra, one over nanostructure (top line) and the other one outside the nanochain (bottom line), are performed in the range of 1050-1925 $cm^{-1}$ (FIG. 3b).

The static measurement points can be seen in optical image of the mapping area. R6G SERS peaks are observed at around 1360 $cm^{-1}$ attributed to $COO^-$ vibration; 1506, 1569, 1649 $cm^{-1}$ related to the C—C ring stretching vibration. Besides these bands, a few more bands, centered at 1126 and 1188 cm-1 attributed to C—$H_x$ in-plane bending, and 1310 $cm^{-1}$ attributed to C—OH stretching vibrations, are also evident. It can be observed from FIG. 3B that the Raman spectra of R6G are observed only at the nanostructure point, whereas only a broad background is observed at the rest of the location. Since the molecule deposited on the Ag-nanoparticles is a fluorescent molecule which, in general, shows a broad fluorescence background spectrum, the presence of a nanochain causes a fluorescent quenching and hence only the Raman spectrum of the molecule was shown. This phenomenon of fluorescent quenching for the molecules attached to the metal surface has been observed. See, for example, E. Dulkeith et al., Phys. Rev. Letts., 89 (2002) 203002-1; P. Anger et al., Phys. Rev. Letts., 96 (2006)

Figure 3C:
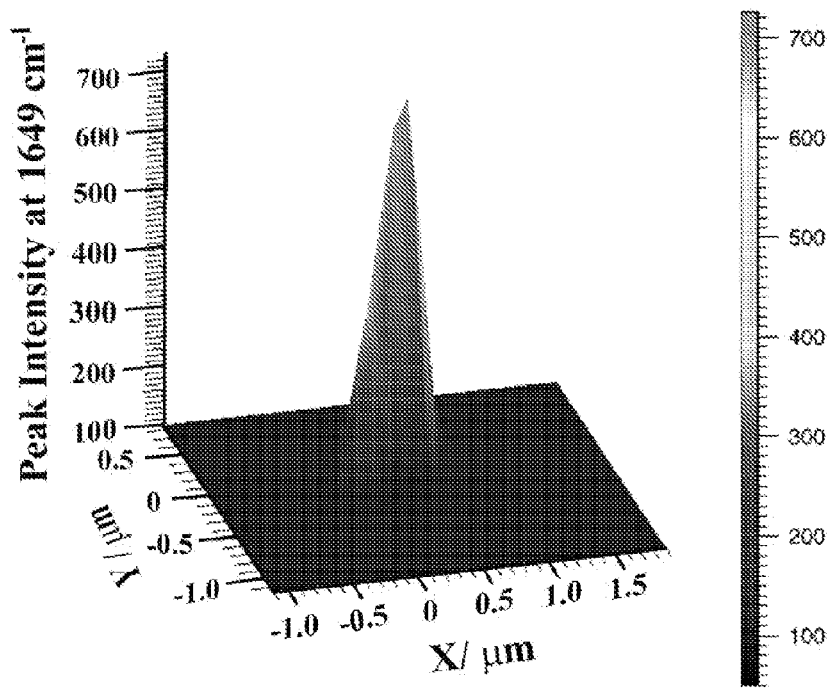
FIG. 3C shows a mapping analysis of the intensity Raman peak at specific wavenumber a649 $cm^{-1}$.

113002-1, each of which is incorporated by reference in its entirety. Micro-Raman XY-mapping measurements were carried out in the range of 1050-1925 cm$^{-1}$ for the area of around 3×2 µm$^2$. The mapping analysis, keeping the R6G peak centered at 1649 cm$^{-1}$ as a reference band, is shown in FIG. 3C. The polarization of incident source is parallel to the nanostructure which is an optimal condition to achieve the maximum SERS signal. The Raman analysis has been executed by selecting the Raman band in the region of 1618 and 1689 cm$^{-1}$. For the mapping analysis, each and every spectra in the region 1618-1689 cm-1 was first baseline corrected and then evaluated after the intensity of the band was centered at 1649 cm-1. The maximum peak intensity is observed only at those points where nanochain structures are present. The remaining area doesn't show any variation regarding this vibrational band. High sensitive, and high signal-to-noise SERS signal are observed for R6G using this device. The observed broadness of the mapping band is due to the convolution of laser beam-width. Considering that the major SERS contribution is from smallest metal nanosphere and the surface area of a Rhodamine6G molecule is about 0.9 nm$^2$, the Raman signal coming from the nanochain can be due to closely packed 100-150 molecules.

If there are metallic nanospheres in self-similar cascade mode, the majority of SERS intensity can come from the vicinity of the smallest nanosphere and the enhancement factor can reach >10$^{12}$. Fine Difference Time Domain (FDTD) simulation can be performed and then compared between the real geometry device fabricated in lab and the ideal device proposed by Dai. See, for example, J. Dai et al., Phys. Rev. B 77 (2008) 115419, which is incorporated by reference in its entirety. The device in self-similar mode keeps functioning even when the device geometry is deformed. In addition, The Stockman used 380 nm laser wavelength which is the best for the silver nanoparticles to simulate the field enhancement whereas 514 nm was used as a SERS spectra excitation wavelength. Considering that the major SERS contribution is from smallest metal nanosphere and the surface area of a Rhodamine6G molecule is about 0.9 nm$^2$, it is estimated that the Raman signal coming from the nanochain is due to 100-150 molecules when closely packed. Taking into consideration all the factors (such as the number of molecules observed under laser spot, laser power, accumulation time, Raman intensity), the enhancement factor using the nanochain device is calculated to be around 5×10$^7$ with respect to the Si.

Figure 4:
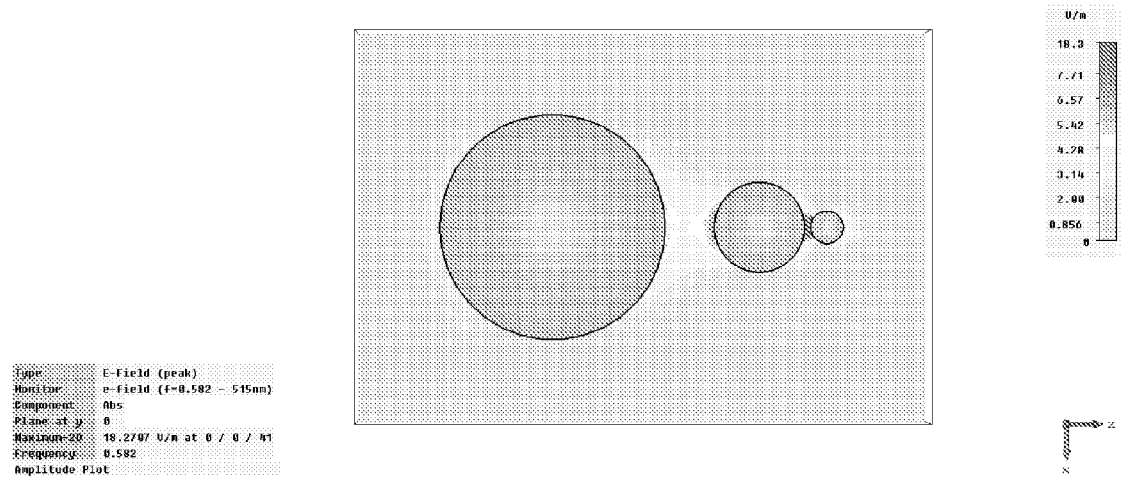
FIG. 4 shows FDTD numerical simulation of a single nanochain.
Figure 5:
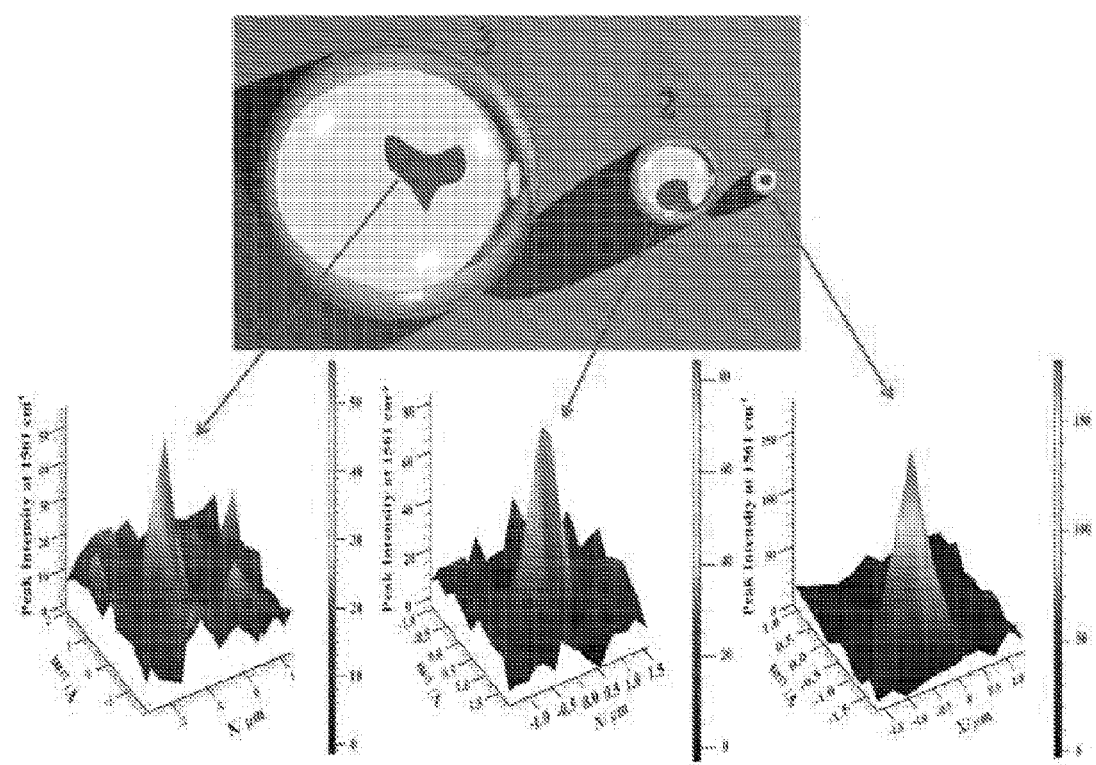
FIG. 5 shows mapping analysis of a nanochain including three nanostructures.
Figure 6A:
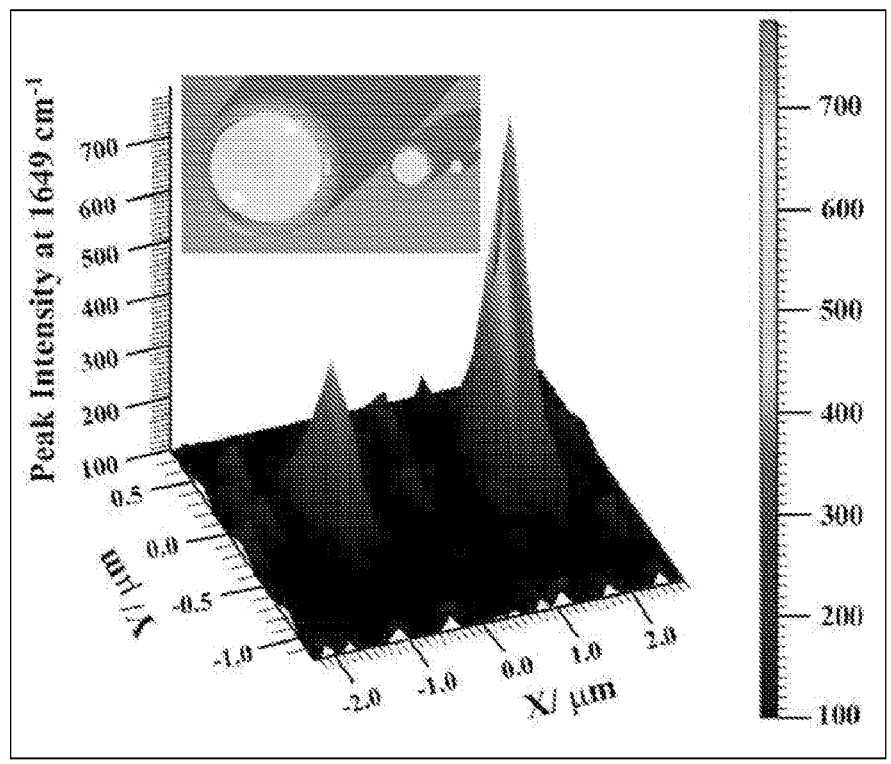
FIGS. 6A-6D show mapping analysis of different nanochain structures (monomer, dimer, trimer, tetramer).
Figure 6B:
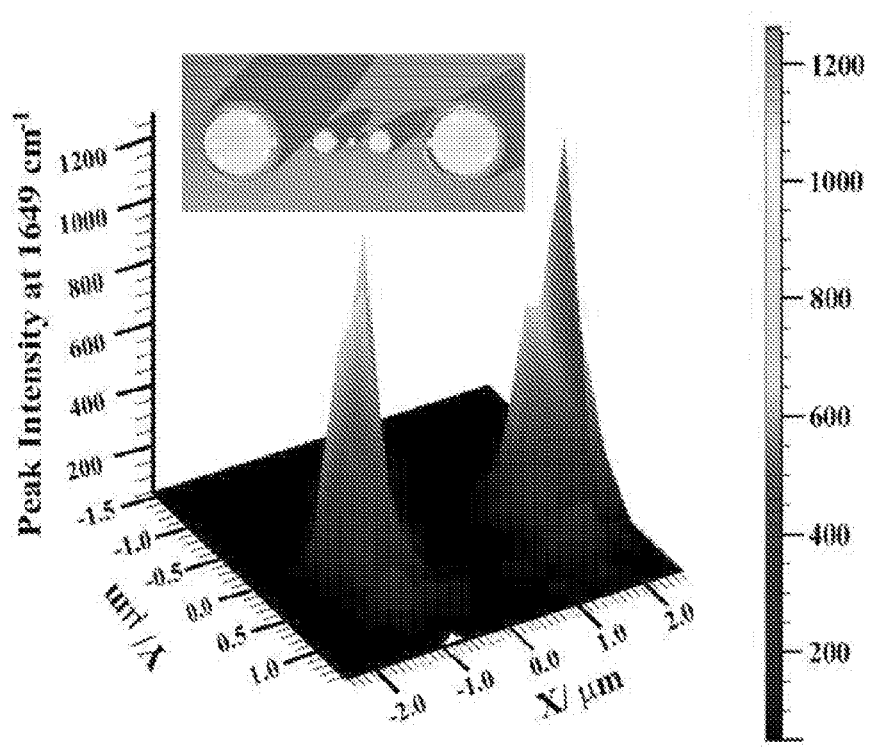
Figure 6C:
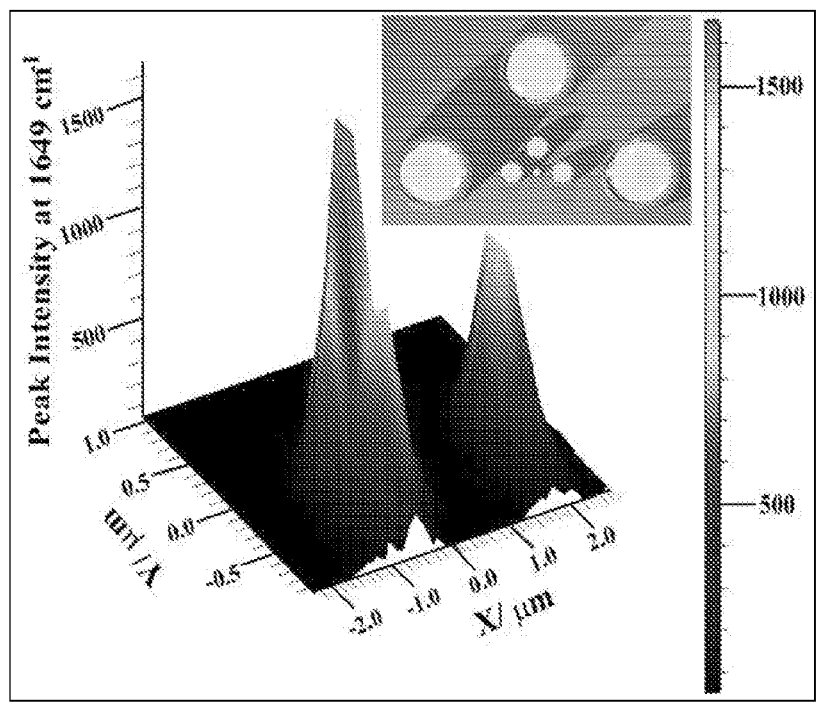
Figure 6D:
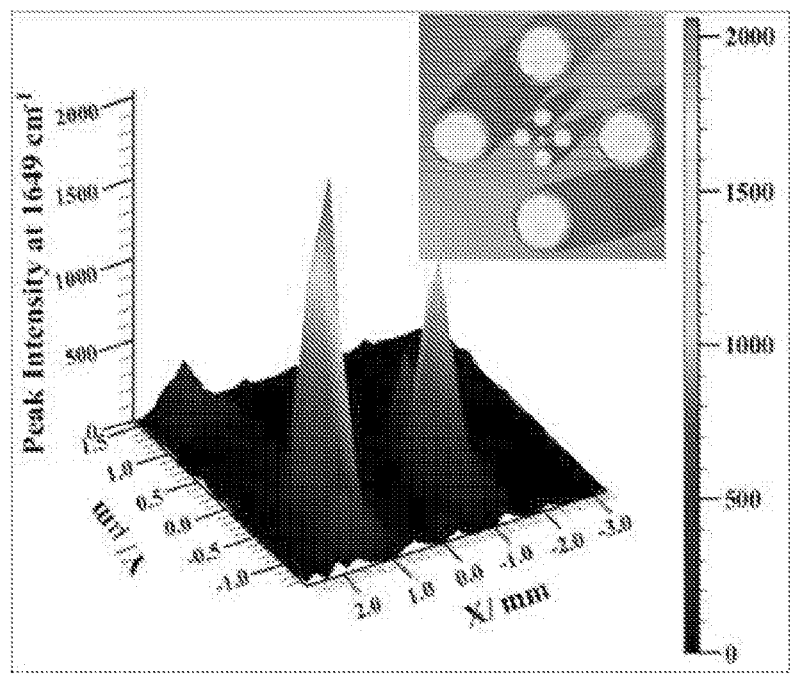

The experimental verification of high sensitivity by varying the position of molecules on self-similar chain device is carried out by depositing the carbon at a known position of the nanochain device. After depositing the carbon on the top of smallest, middle and biggest nanosphere, individually, the micro-Raman measurements were performed. 3D-Raman intensity analysis related to the C—C vibration centred at 1561 cm-1 is performed for each and every spectrum in the mapping area by selecting the base line corrected curve in the region of 1400-1750 cm-1. It can be noticed that the band intensity is maximum for the sample on which carbon is deposited on the smallest nanosphere. The intensity trend of $I_{smallest} > I_{middle} > I_{biggest}$ is observed. These measurements confirm the detection sensitivity of this device. See FIGS. 4 and 5.

The measurements are performed to verify the dependency of Raman signal by increasing the number of nanochains, shown in FIGS. 6A-6D and FIGS. 10A-10C. R6G monolayer is deposited over the device and the Raman spectra were taken with the same Raman parameters. The mapping analysis results, shown in FIGS. 6A-6D, is performed for the Raman band centered at 1649 cm$^{-1}$. In the inset, the associated nanochain structure is shown. 3D mapping spectra in FIGS. 6A-6D illustrate the increase in Raman signal from 700 for single nanochain to around 2000 counts for four-nanochain structure.

Figure 7A:
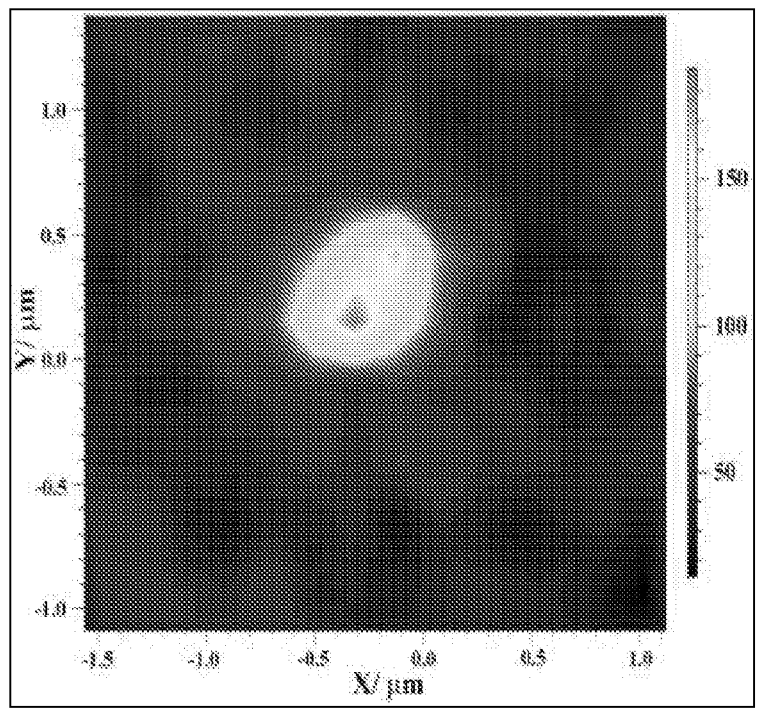
FIG. 7A shows mapping analysis for a nanochain with three nanospheres.
Figure 7B:
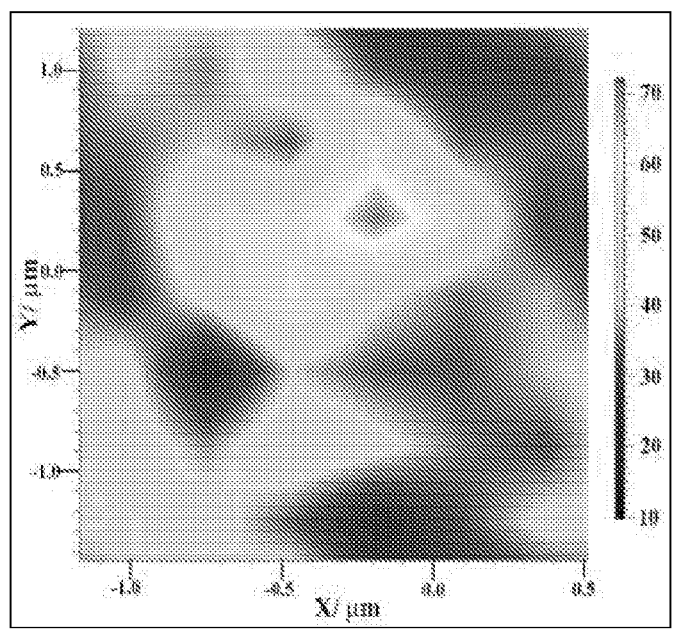
FIG. 7B shows mapping analysis for a nanochain with two nanospheres.
Figure 8A:
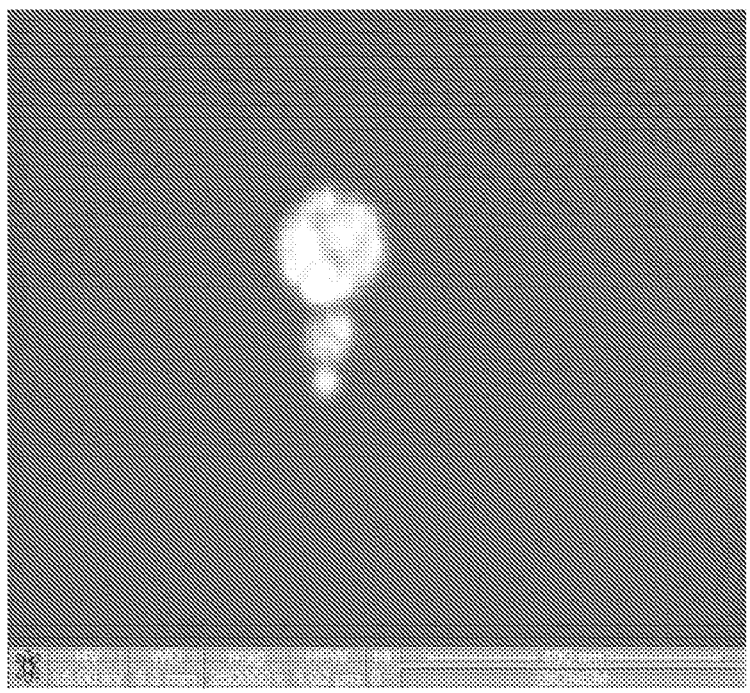
FIGS. 8A-8B show SEM images of nanostructures with different sizes.
Figure 8B:
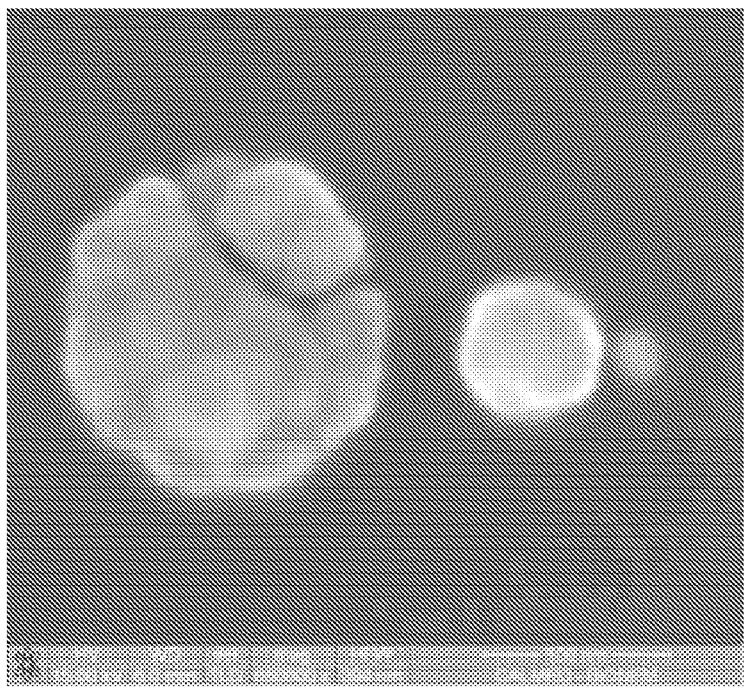
Figure 9A:
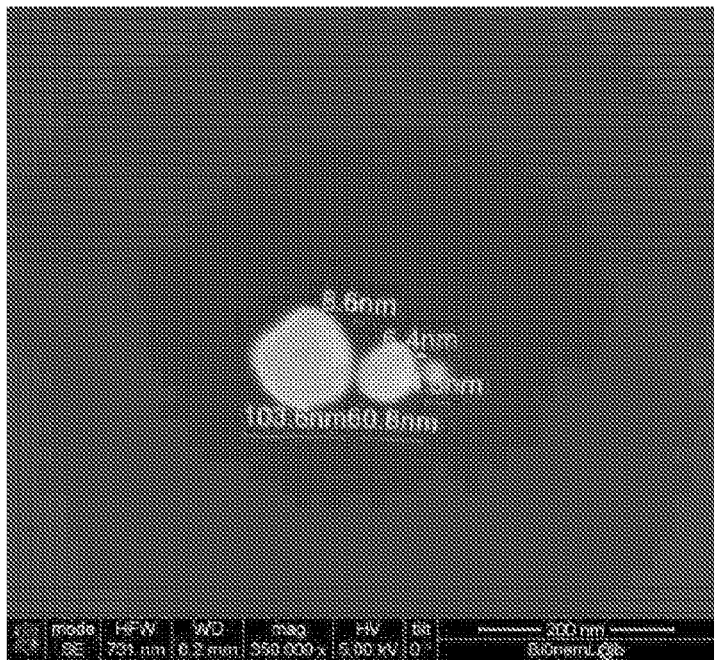
FIGS. 9A-9B show SEM images of nanostructures with different sizes.
Figure 9B:
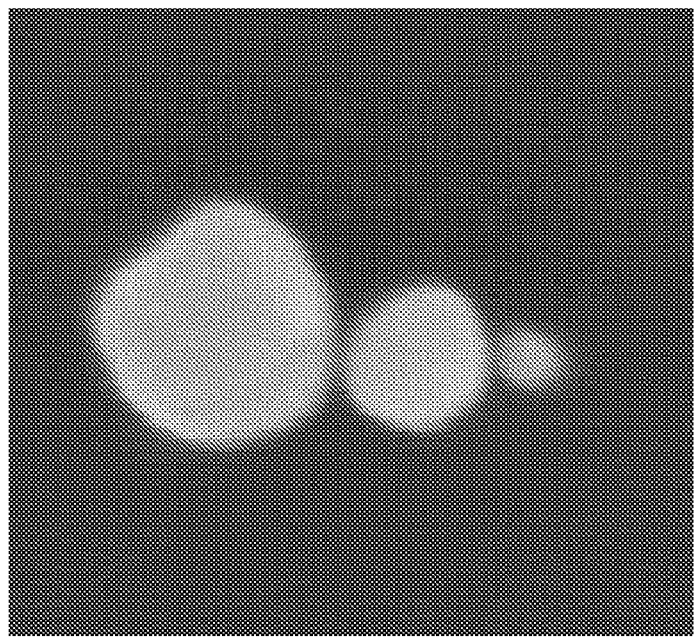

Raman intensity for nanochains with three nanospheres and two nanospheres was compared. The results show the validity of a device including three nanospheres in cascade mode. For such verification, monolayer benzenethiol molecule is deposited over a device with two nanospheres and three nanospheres. Micro-Raman mapping analysis for the Raman band centred at 1584 cm$^{-1}$ is carried out for both samples, shown in FIGS. 7A-7B. The peak intensity increase and signal to noise ratio improvement were observed for the device with three nanospheres.

To prepare a chip array, the steps of preparing each pixel are repeated. This can be done automatically with electron beam writing strategy. The noble metal reduction is done in parallel when the device is dipped in AgNO$_3$/HF solution.

Figure 11:
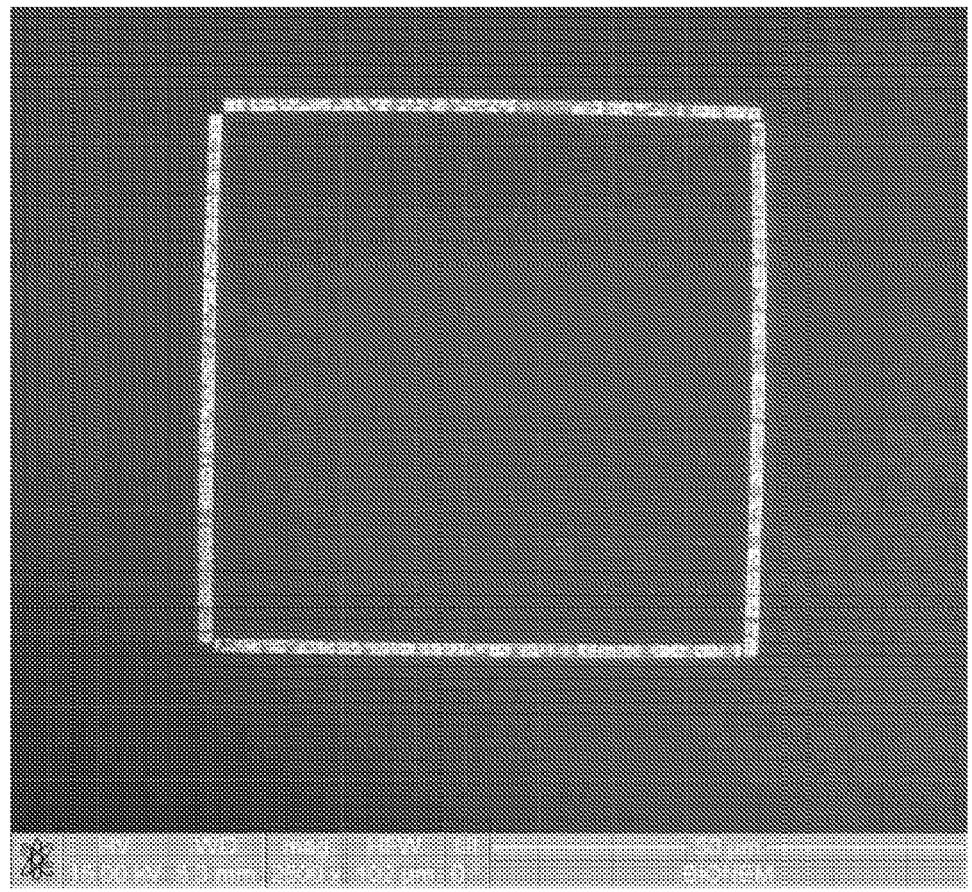
FIG. 11 shows an SEM image of a device including a plurality of pixels.
Figure 12:
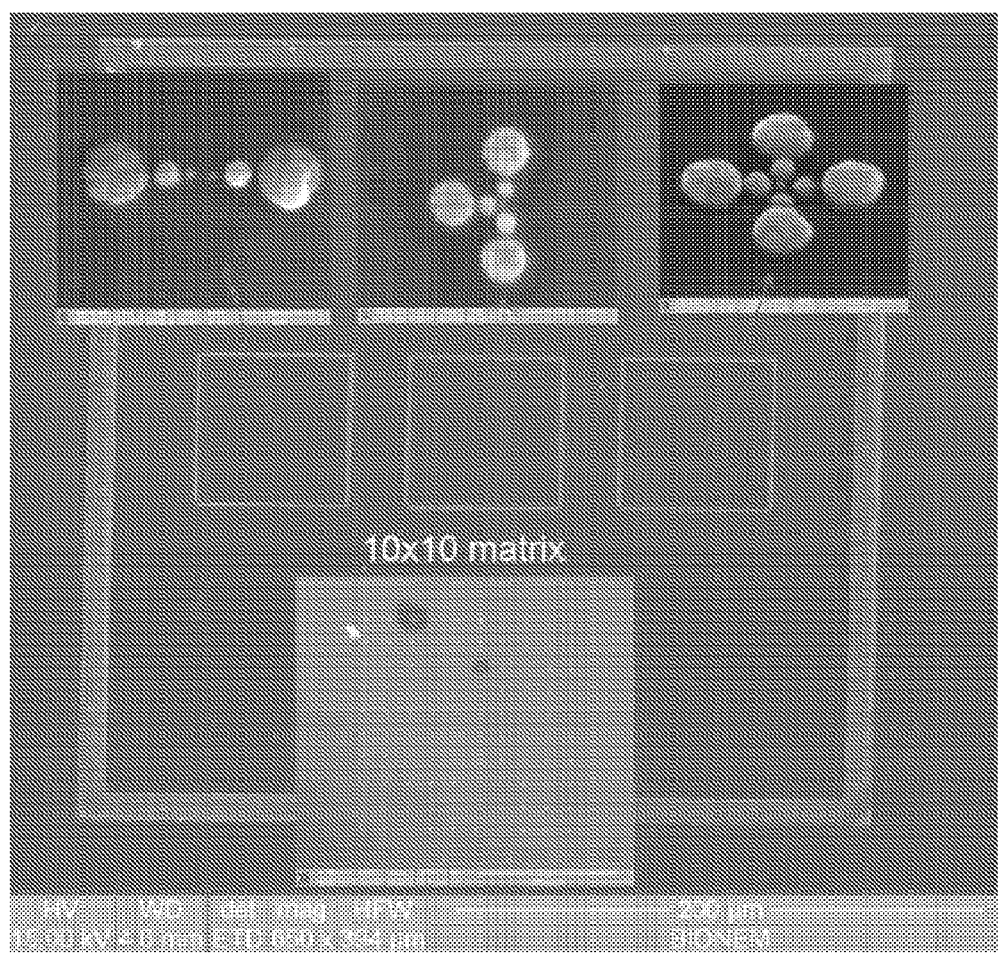
FIG. 12 shows SEM images of a device including a plurality of pixels and SEM images of three different pixels typology (dimers, trimers, tetramers).
Figure 13A:
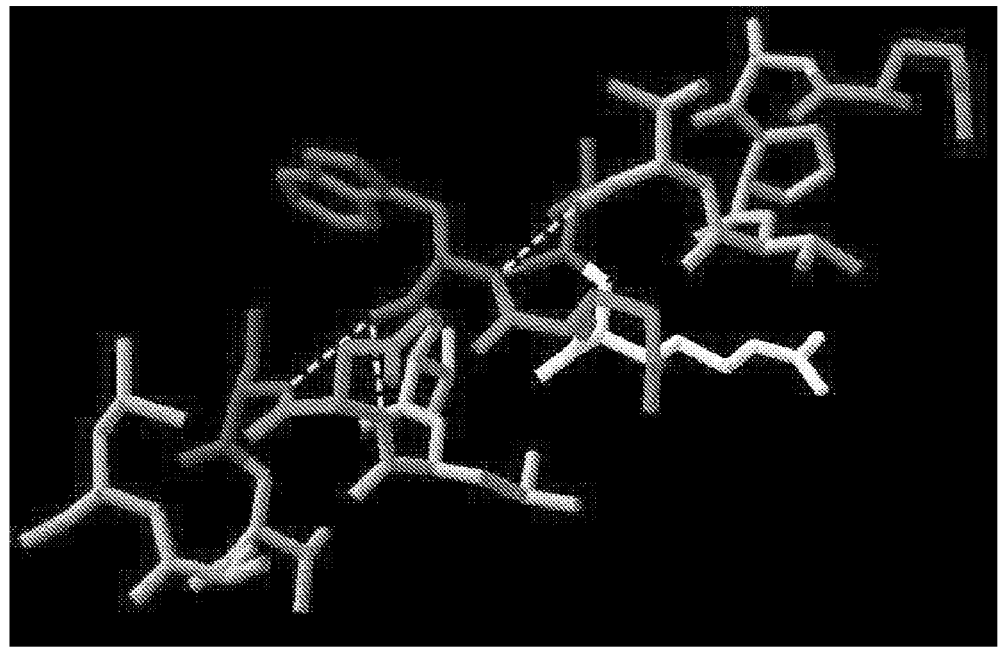
FIGS. 13A-13B show a wild type and a mutated peptide W1837 from gene BRCA1 in breast cancer.
Figure 13B:
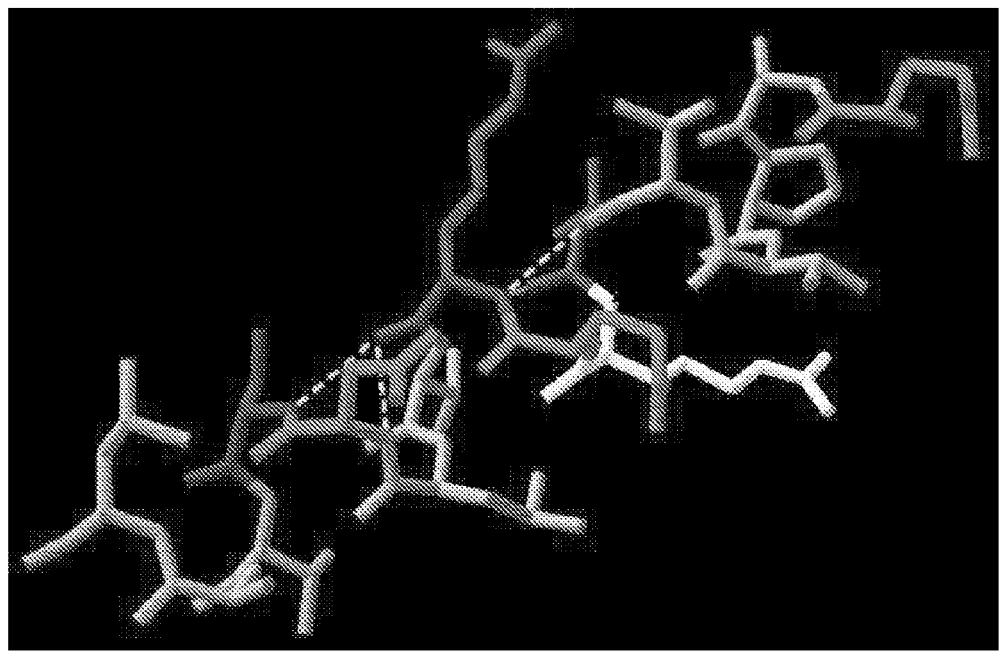
Figure 14A:
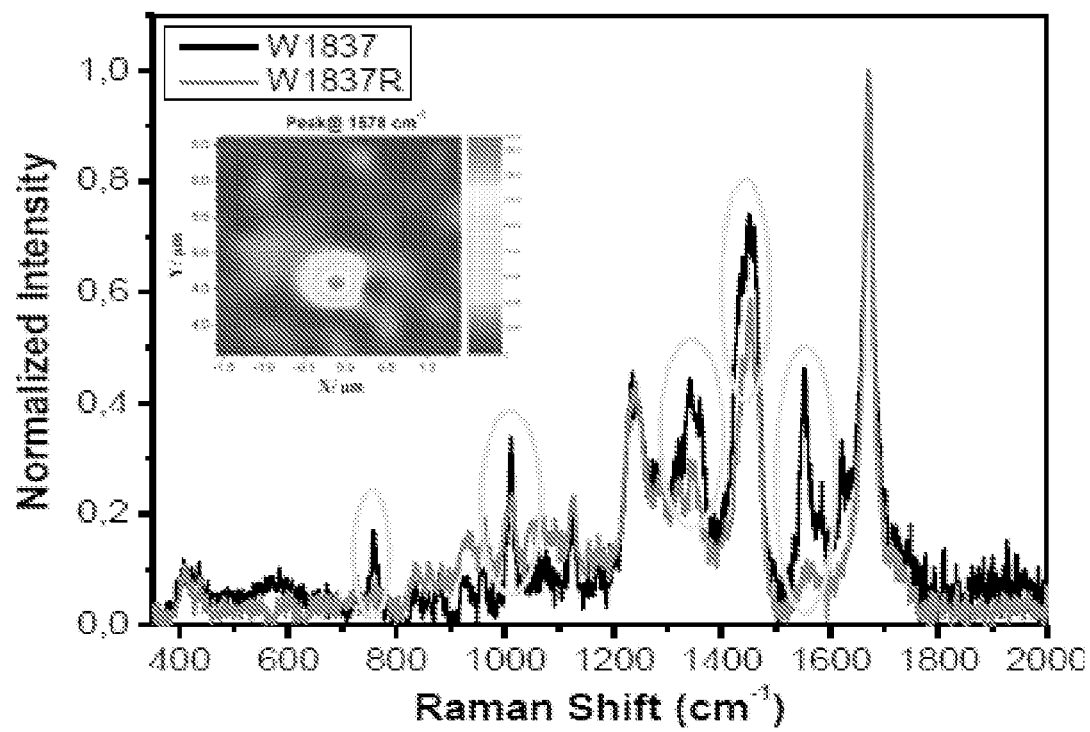
FIGS. 14A-14B shows Raman spectra of W1837 peptide on a device including nanochains.
Figure 14B:
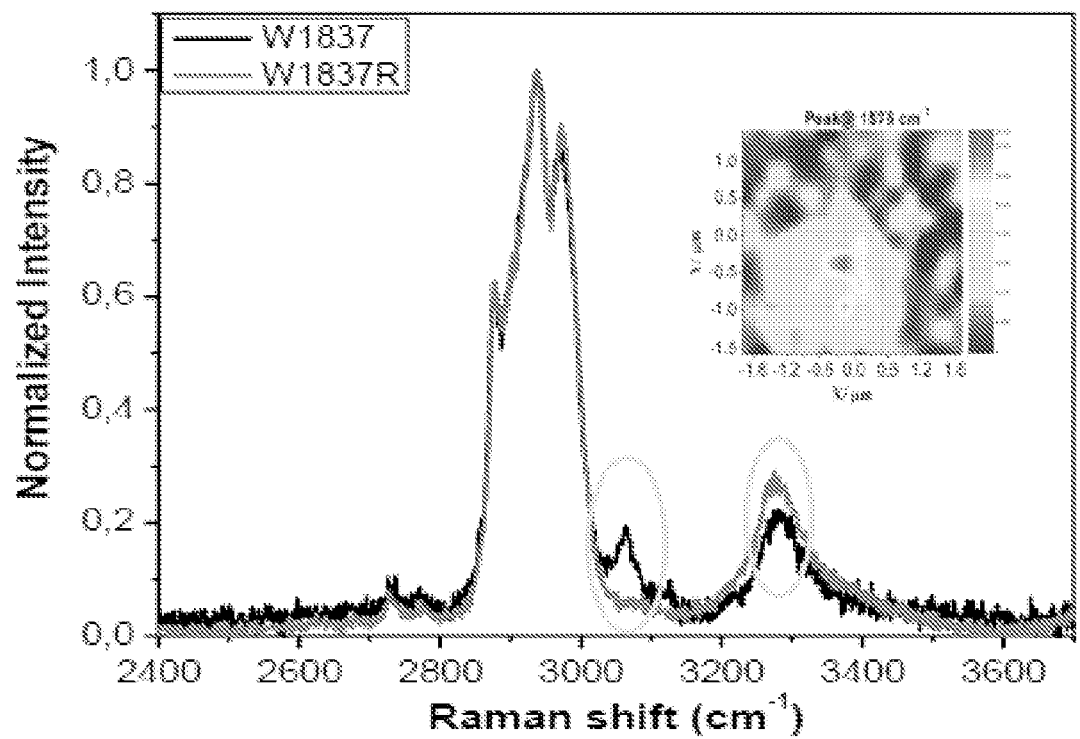
Figure 15A:
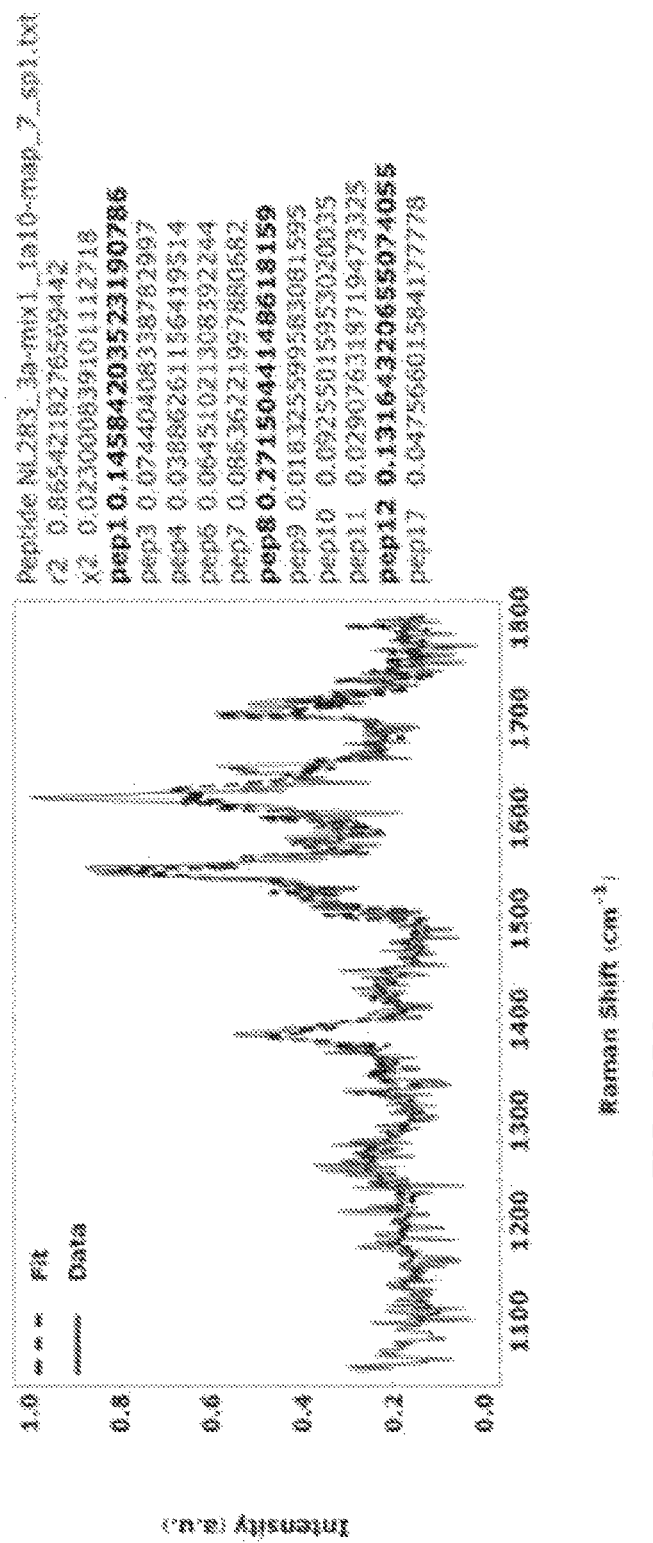
FIGS. 15A-15C show Raman spectra of a specific pixel from a mixture of 22 peptides on a device including nanochains.
Figure 15B:
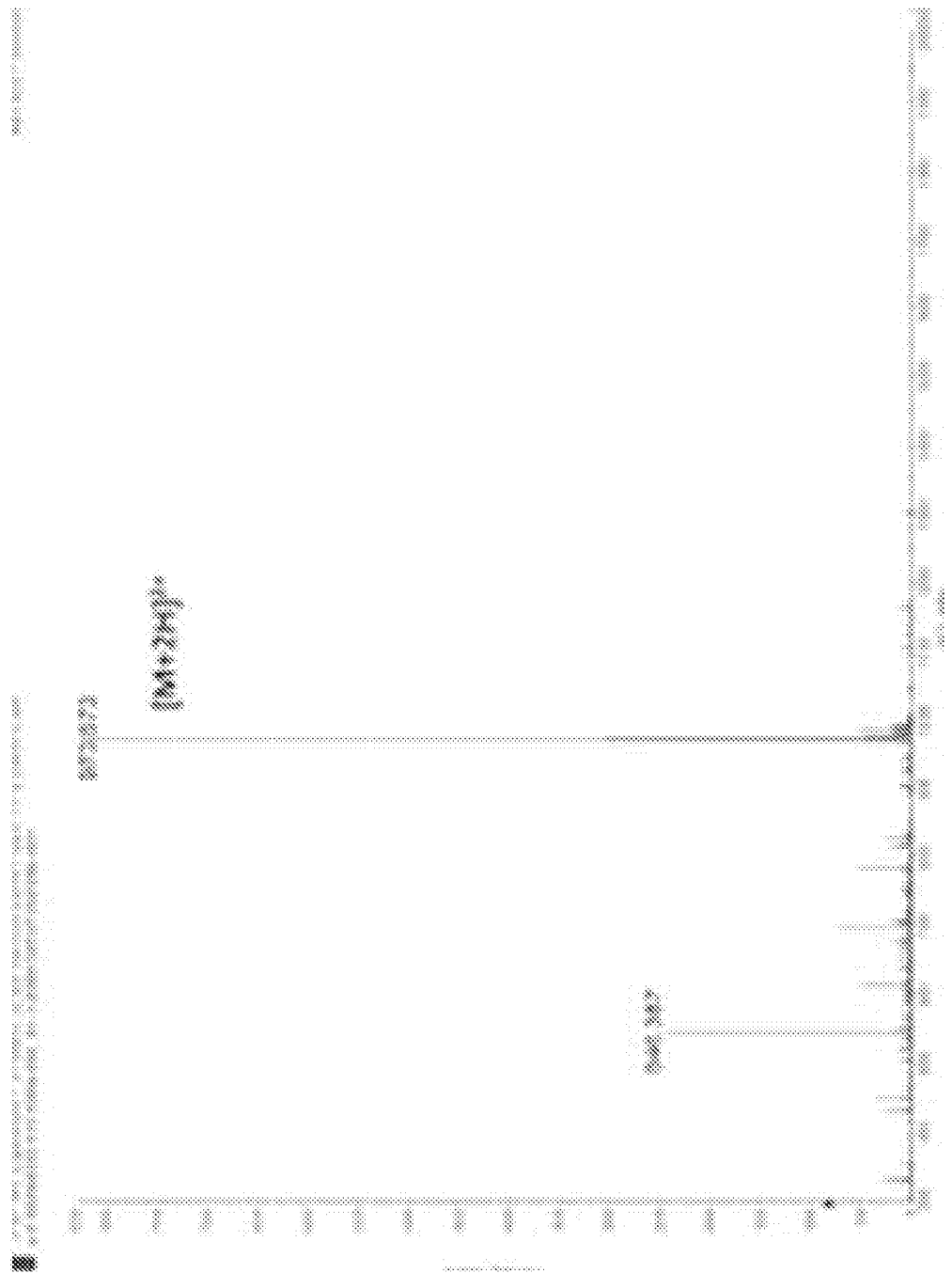
Figure 15C:
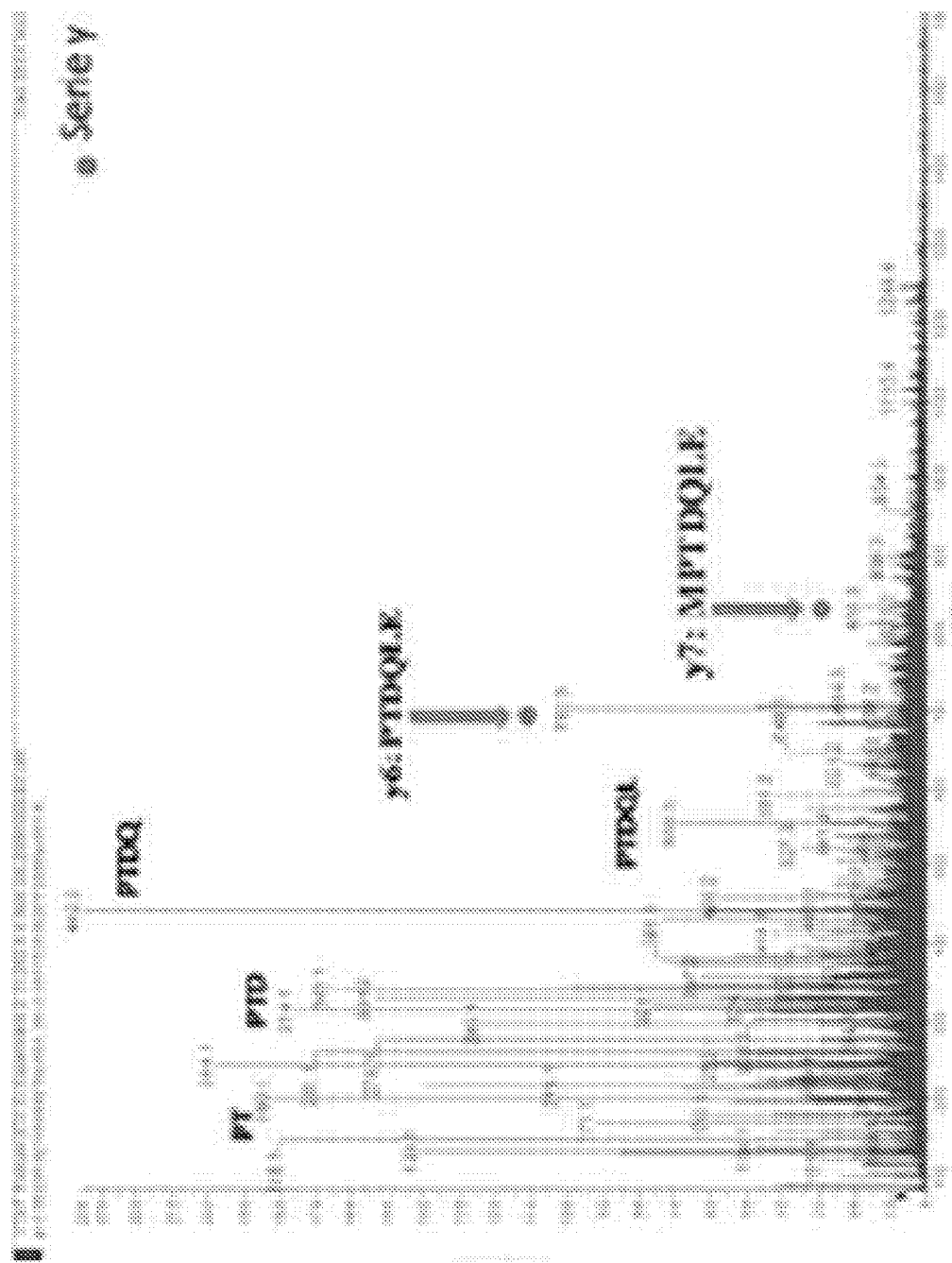

FIGS. 8A-8B to FIGS. 10A-10C show SEM images of nanochains. FIG. 11 shows an SEM image of a device including a plurality of pixels. FIG. 12 shows SEM images of a device including a plurality of pixels and SEM images of three pixels. FIGS. 13A-13B show a wild type and a mutated gene BRCA1 in breast cancer. FIGS. 14A-14B show Raman spectra of W1837 peptide on a device including nanochains. FIGS. 15A-15B shows Raman spectra of a mixture of 22 peptides on a device including nanochains.

Other embodiments are within the scope of the following claims.

What is claimed is:

1. A device for detecting an analyte in a sample comprising:
   an array including a plurality of pixels, each pixel including a nanochain comprising:
      a first nanostructure,
      a second nanostructure, and
      a third nanostructure,
         wherein size of the first nanostructure is larger than that of the second nanostructure, and size of the second nanostructure is larger than that of the third nanostructure, and
         wherein the first nanostructure, the second nanostructure, and the third nanostructure are positioned on a substrate such that when the nanochain is excited by an energy, an optical field between the second nanostructure and the third nanostructure is stronger than an optical field between the first nanostructure and the second nanostructure,
   wherein the array is configured to receive a sample; and
   a detector arranged to collect spectral data from a plurality of pixels of the array.

2. The device of claim 1, wherein the first nanostructure includes a metal, the second nanostructure includes a metal, and the third nanostructure includes a metal.

3. The device of claim 1, wherein the nanostructure includes silver, gold, platinum, or aluminum.

4. The device of claim 1, wherein the second nanostructure is positioned between the first nanostructure and the third nanostructure.

5. The device of claim 1, wherein the distance between the first nanostructure and the second nanostructure is less than the diameter of the second nanostructure.

6. The device of claim 1, wherein the distance between the second nanostructure and the third nanostructure is less than the diameter of the third nanostructure.

7. The device of claim 1, wherein the device includes 10 by 10 pixels.

8. The device of claim 1, wherein the distance between two pixels is at least 1 µm.

9. The device of claim 1, wherein each pixel delivers spectral data for at least one analyte.

10. The device of claim 1, wherein each pixel is capable of detecting at least two different kinds of analytes.

11. The device of claim 1, wherein the device is capable of detecting at least 20 different kinds of analytes.

12. The device of claim 1, wherein the analyte is detectable by Raman spectrum.

13. The device of claim 1, wherein the analyte is a peptide.

14. The device of claim 1, wherein the device is capable of detecting a single molecule.

15. The device of claim 1, wherein the first nanostructure is a nanosphere, the second nanostructure is a nanosphere, and the third nanostructure is a nanosphere.

16. A method for detecting an analyte comprising:
contacting an analyte with an array including a plurality of pixels, each pixel including a nanochain comprising:
a first nanostructure,
a second nanostructure, and
a third nanostructure,
wherein size of the first nanostructure is larger than that of the second nanostructure, and size of the second nanostructure is larger than that of the third nanostructure, and
wherein the first nanostructure, the second nanostructure, and the third nanostructure are positioned on a substrate such that when the nanochain is excited by an energy, an optical field between the second nanostructure and the third nanostructure is stronger than the optical field between the first nanostructure and the second nanostructure; and
collecting spectral data from a plurality of pixels of the array.

17. The method of claim 16, further comprising taking Raman spectrum of the nanochain.

18. The method of claim 16, wherein the analyte includes a peptide.

19. The method of claim 16, wherein the first nanostructure includes a metal, the second nanostructure includes a metal, and the third nanostructure includes a metal.

20. The method of claim 16, further comprising detecting a single molecule.

* * * * *